United States Patent
Chin et al.

(10) Patent No.: US 12,097,364 B2
(45) Date of Patent: Sep. 24, 2024

(54) APPARATUS, SYSTEMS, AND METHODS FOR PERCUTANEOUS PNEUMATIC CARDIAC ASSISTANCE

(71) Applicant: PercAssist, Inc., Santa Clara, CA (US)

(72) Inventors: Albert K. Chin, Palo Alto, CA (US); Gerardo Noriega, Mountain View, CA (US); William Hsu, Santa Clara, CA (US)

(73) Assignee: PERCASSIST, INC., Santa Clara, CA (US)

( * ) Notice: Subject to any disclaimer, the term of this patent is extended or adjusted under 35 U.S.C. 154(b) by 323 days.

(21) Appl. No.: 17/411,928

(22) Filed: Aug. 25, 2021

(65) Prior Publication Data
US 2021/0379357 A1 Dec. 9, 2021

Related U.S. Application Data

(63) Continuation of application No. PCT/US2020/019974, filed on Feb. 26, 2020.
(Continued)

(51) Int. Cl.
*A61M 60/295* (2021.01)
*A61M 60/104* (2021.01)
(Continued)

(52) U.S. Cl.
CPC ........ *A61M 60/295* (2021.01); *A61M 60/104* (2021.01); *A61M 60/178* (2021.01);
(Continued)

(58) Field of Classification Search
CPC .............. A61M 60/295; A61M 60/104; A61M 60/405; A61M 60/515; A61M 60/596;
(Continued)

(56) References Cited

U.S. PATENT DOCUMENTS

| 4,536,893 A | 8/1985 | Parravicini |
| 4,771,765 A | 9/1988 | Choy et al. |

(Continued)

FOREIGN PATENT DOCUMENTS

| BE | 1020432 A3 * | 10/2013 | ......... A61B 5/02405 |
| CN | 107532168 A | 1/2018 | |

(Continued)

OTHER PUBLICATIONS

"Cannula care".Northumbria Healthcare. Jul. 2016. Accessed online. <https://www.northumbria.nhs.uk/sites/default/files/images/15.09.15_8.pdf> (Year: 2016).*

(Continued)

*Primary Examiner* — Tammie K Marlen
*Assistant Examiner* — Maria Catherine Anthony
(74) *Attorney, Agent, or Firm* — Wilson Sonsini Goodrich & Rosati

(57) ABSTRACT

A cardiac assist system includes a pneumatic effector which is implanted beneath a pericardial sac and over a myocardial surface overlying the patient's left ventricle. A port is implanted and receives a percutaneously introduced cannula. The port is connected to supply a driving gas received from the cannula to the pneumatic effector. An external drive unit includes a pump assembly and control circuitry which operate the pump to actuate the pneumatic effector in response to the patient's sensed heart rhythm. A connecting tube has a pump end connected to the pump and a percutaneous port-connecting end attached to the implantable port.

30 Claims, 9 Drawing Sheets

Related U.S. Application Data

(60) Provisional application No. 62/810,866, filed on Feb. 26, 2019.

(51) Int. Cl.
*A61M 60/178* (2021.01)
*A61M 60/216* (2021.01)
*A61M 60/405* (2021.01)
*A61M 60/515* (2021.01)
*A61M 60/569* (2021.01)
*A61M 60/841* (2021.01)
*A61M 60/845* (2021.01)

(52) U.S. Cl.
CPC ........ *A61M 60/216* (2021.01); *A61M 60/405* (2021.01); *A61M 60/515* (2021.01); *A61M 60/569* (2021.01); *A61M 60/841* (2021.01); *A61M 60/845* (2021.01); *A61M 2230/04* (2013.01)

(58) Field of Classification Search
CPC .............. A61M 60/841; A61M 60/845; A61M 60/289; A61M 60/468; A61M 60/191; A61M 60/839; A61M 60/865; A61M 60/13; A61M 2230/04; A61M 2039/0244
See application file for complete search history.

(56) References Cited

U.S. PATENT DOCUMENTS

| | | | |
|---|---|---|---|
| 4,925,443 A * | 5/1990 | Heilman | A61M 60/538 600/16 |
| 4,957,477 A | 9/1990 | Lundback | |
| 5,084,010 A | 1/1992 | Plaia et al. | |
| 5,713,954 A | 2/1998 | Rosenberg et al. | |
| 6,042,532 A | 3/2000 | Freed et al. | |
| 6,120,492 A | 9/2000 | Finch et al. | |
| 6,238,334 B1 | 5/2001 | Easterbrook, III et al. | |
| 6,432,039 B1 | 8/2002 | Wardle | |
| 6,585,635 B1 * | 7/2003 | Aldrich | A61M 60/187 600/16 |
| 6,602,182 B1 | 8/2003 | Milbocker | |
| 7,468,029 B1 | 12/2008 | Robertson, Jr. | |
| 8,092,363 B2 | 1/2012 | Leinsing et al. | |
| 8,509,894 B2 | 8/2013 | Forsell | |
| 9,259,318 B2 | 2/2016 | Laham et al. | |
| 10,220,128 B1 | 3/2019 | Robinson et al. | |
| 10,391,216 B2 | 8/2019 | Wildhirt et al. | |
| 2001/0041821 A1 * | 11/2001 | Wilk | A61M 60/531 600/16 |
| 2002/0065449 A1 * | 5/2002 | Wardle | A61F 2/2481 600/37 |
| 2002/0072679 A1 | 6/2002 | Schock et al. | |
| 2002/0165535 A1 | 11/2002 | Lesh et al. | |
| 2003/0032936 A1 | 2/2003 | Lederman | |
| 2003/0187460 A1 | 10/2003 | Chin et al. | |
| 2006/0074484 A1 | 4/2006 | Huber et al. | |
| 2007/0049806 A1 * | 3/2007 | Adams | A61B 5/318 604/65 |
| 2007/0073218 A1 | 3/2007 | Lau et al. | |
| 2007/0093720 A1 | 4/2007 | Fischell et al. | |
| 2008/0064917 A1 | 3/2008 | Bar et al. | |
| 2008/0275294 A1 * | 11/2008 | Gertner | A61F 2/2481 600/37 |
| 2008/0275295 A1 | 11/2008 | Gertner | |
| 2009/0062734 A1 | 3/2009 | Keith et al. | |
| 2011/0275883 A1 | 11/2011 | Peters | |
| 2017/0258521 A1 | 9/2017 | Asirvatham et al. | |
| 2017/0368246 A1 | 12/2017 | Criscione et al. | |
| 2019/0076250 A1 | 3/2019 | Hjelle et al. | |

FOREIGN PATENT DOCUMENTS

| | | | |
|---|---|---|---|
| EP | | 2111800 A1 | 10/2009 |
| WO | WO-9805289 A1 | | 2/1998 |
| WO | WO-2017161166 A1 | | 9/2017 |
| WO | WO-2020176670 A1 | | 9/2020 |

OTHER PUBLICATIONS

"Cannula Care", Northumbria Healthcare, Jul. 2016; accessed online at https://www.northumbria.nhs.uk/sites/default/files/images/15.09.15_8.pdf.

Gerald A. Jones, et al., Fundamental Studies on Maintenance of the Circulation in Cardiac Asystole by the Mechanocardiac Pulsator, Chestnet, Feb. 1961, pp. 207-217.

International Search Report for PCT/US2020/019974 on Jun. 2, 2020.

EP20762552.6 European Extended Search Report dated Oct. 26, 2022.

EP23197532.7 Partial European Search Report dated Mar. 15, 2024.

* cited by examiner

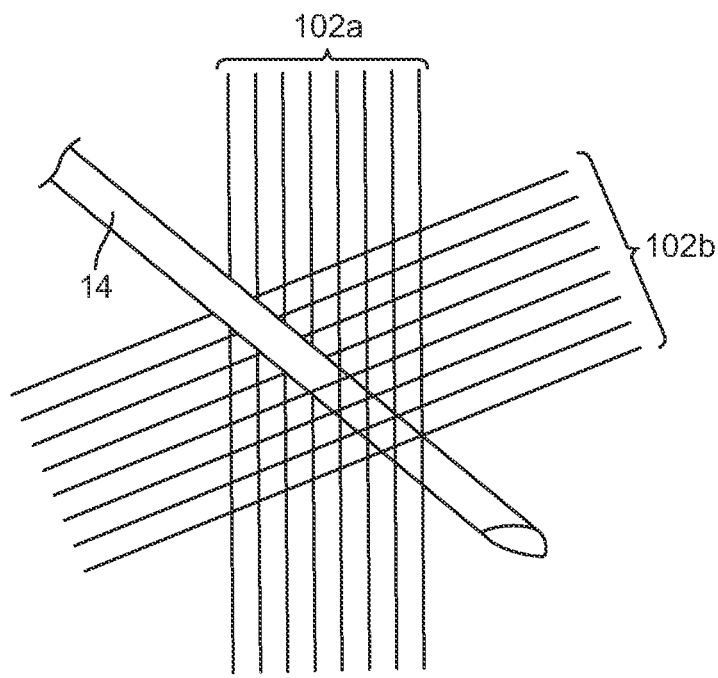
FIG. 6
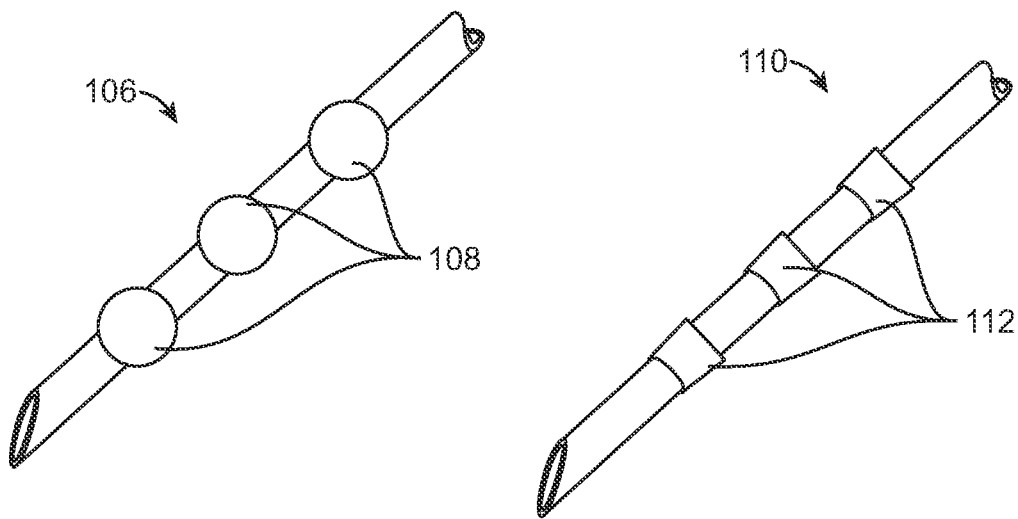
FIG. 7A
FIG. 7B

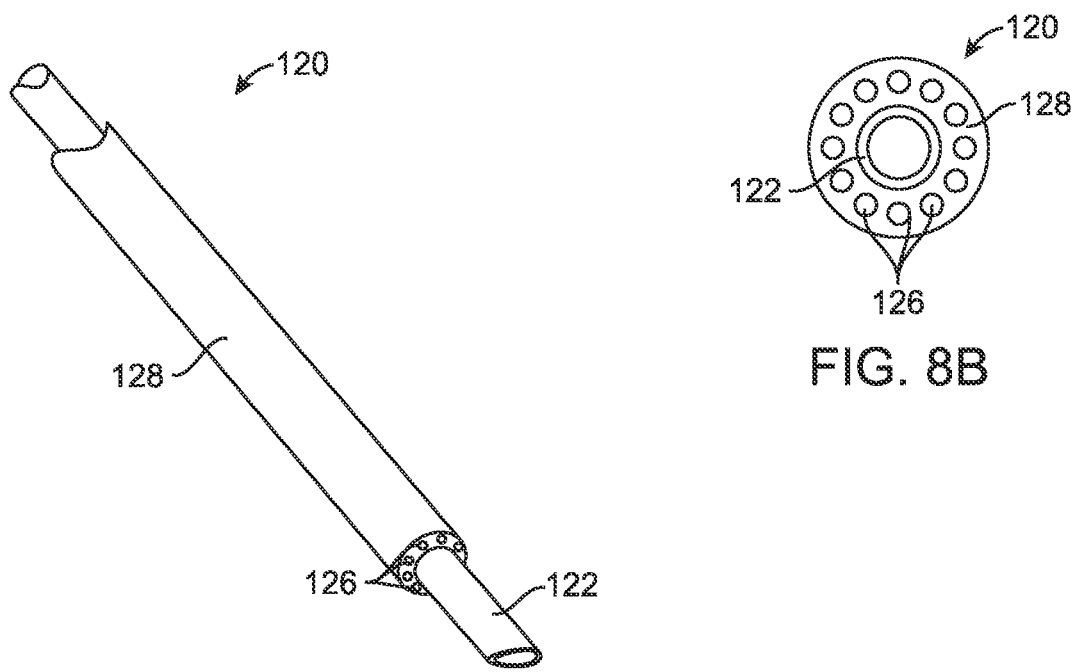
FIG. 8A
FIG. 8B
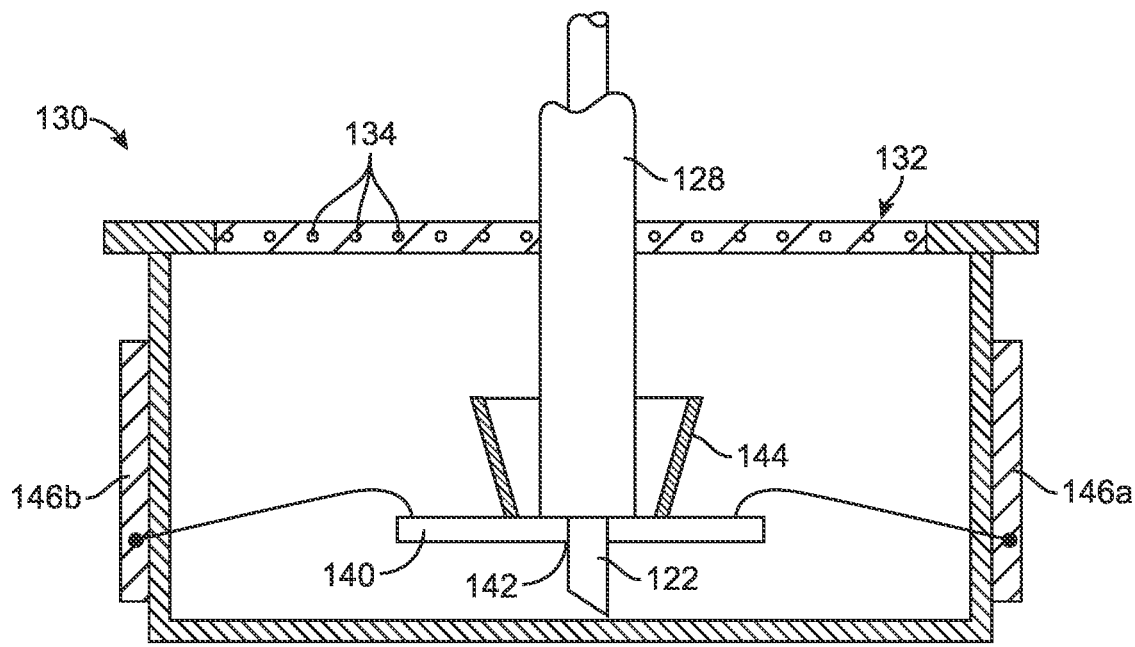
FIG. 9

APPARATUS, SYSTEMS, AND METHODS FOR PERCUTANEOUS PNEUMATIC CARDIAC ASSISTANCE

CROSS-REFERENCE TO RELATED APPLICATIONS

This application is a continuation of PCT Application No. PCT/US20/19974, filed Feb. 26, 2020, which claims the benefit of US Provisional No. 62/810,866, filed Feb. 26, 2019, the entire content of each are incorporated herein by reference.

BACKGROUND OF THE INVENTION

1. Field of the Invention

The present invention relates generally to medical devices, systems, and methods. More particularly, the present invention relates to systems for providing cardiac assist to patients suffering from late stage heart failure.

A variety of ventricular assist devices (VADs) have been proposed for use in supporting blood circulation in patients suffering from severe heart failure. VADs are also used to keep patients alive until a donor heart is available for transplantation as a "bridge to transplant." In the United States, as many as 50,000 patients per year require heart transplantation due to end stage heart failure. Donor hearts are only available for 2,000 to 2,500 patients per year. Many patients who are unable to receive transplants can survive by receiving a VAD.

Placement of presently available VADs, however, often requires a large surgical incision, typically either a sternotomy or thoracotomy. It is difficult for a patient in heart failure to undergo such a large surgical procedure. While a number of minimally invasive VADs have been proposed, such as intravascular rotary pumps and external compressive devices, such minimally invasive systems usually require a large transcutaneous "umbilical cord" to provide the power to drive the implanted pump assist component. Such cords are inconvenient, uncomfortable, and present substantial risk of infection. Moreover, when infected, removal of the large cords often requires surgical intervention.

For these reasons, it would be desirable to provide improved apparatus, systems and methods for providing cardiac assist to patients suffering from late stage heart failure. It would be particularly desirable to provide such systems which can be implanted by subxiphoid and other established minimally invasive routes. It would be further desirable to provide VAD systems having percutaneous connectors which reduce the risk of infection and which, if they become infected, are easier to replace and disinfect. At least some of these requirements will be met by the inventions described and claimed herein.

2. Description of the Background Art

Relevant patents and publications include US2019/0076250; US2008/0275295; US2007/0073218; U.S. Pat. Nos. 10,391,216; 10,220,128; 9,259,318; 8,092,363; 7,468,029; 6,602,182; 6,432,039; 6,238,334; 5,713,954; 4,957,477; and WO1998/005289.

BRIEF SUMMARY OF THE INVENTION

The present invention provides a minimally invasive cardiac assist device for patients suffering from heart failure or other compromised cardiac function. The device comprises an implantable cardiac assist catheter, typically configured to be advanced over a guidewire to a position in the patient's pericardial sac between a myocardial surface and an inner surface of the pericardium. The implantable cardiac assist catheter has a balloon or other pneumatic effector at its distal end, and an external drive unit is usually provided to synchronize balloon inflation with ventricular contractions of the patient's natural cardiac cycle to compress the heart and provide ventricular assistance, thereby increasing the patient's cardiac output. The relative inflexibility of the fibrous pericardial sac provides a restrictive constraint that causes the inflating balloon to compress the ventricle. In addition, the sternum also overlies the heart and provides a bony enclosure to enhance cardiac compression upon balloon inflation. The cardiac assist device may be used with a sensor to obtain an electrocardiographic signal for synchronized balloon inflation.

The intrapericardial cardiac assist catheter may be anchored solely at the point of entry in the pericardium. Alternatively, it may enter the pericardium near the apex of the heart, and exit the pericardium more superiorly, towards the base of the heart, and an expanding anchor such as a small balloon may be present near the distal tip of the catheter, residing outside the pericardium and maintaining the position of the ventricular compression balloon. The ventricular compression balloon may be elliptical in shape, with a length sized to extend along the major portion of the ventricular cavity. The ventricular compression balloon may be inflated with fluid, either gas or liquid, usually being a gas in order to decrease the inflation/deflation times. A gas may be preferred, as it allows a fast response time for balloon inflation and balloon deflation. The frequency of balloon inflation should be equal to a physiologic heart rate, approximately 70 bpm. A small reservoir may be attached to the proximal end of the catheter. One surface of the reservoir may contain a septum or other elastic portion through which a needle may be inserted for balloon inflation, while sealing against the inserted needle. Alternatively, the entire reservoir may be constructed of elastic material that self-seals against needle punctures. Following catheter placement, the reservoir may be implanted subcutaneously via a small skin incision, cardiac assist and oriented such that the elastic surface faces out towards the skin. The balloon catheter and attached subcutaneous reservoir remain implanted while an inflation pump, controller and battery reside external to the patient's skin, with a transcutaneous needle used to inflate and deflate the ventricular compression balloon via the implanted reservoir. This configuration facilitates pump and battery replacement, while decreasing the potential for catheter infection, as a small diameter needle traverses the skin. The needle puncture site may also be changed periodically to decrease the potential for needle tract infection.

The ventricular compression balloon may be inflated and deflated by means of an external battery-operated pump that resides outside of the patient's body. The pump may be bi-directional in flow, with an attached fluid reservoir; or in the case of air inflation of the ventricular compression balloon, the pump inlet and outlet may vent directly to room air. Ventricular compression balloon inflation is synchronized to the cardiac cycle by means of an electrical sensor that senses the patient's ECG (electrocardiographic) signal and initiates balloon inflation at the start of the QRS complex. Patient ECG sensing may be performed via the conductive needle from the external unit that punctures the patient's skin to perform balloon inflation. Alternatively, ECG electrodes or other sensors may be disposed in the implantable port and/or catheter, and the needle used to provide connection to ECG circuitry in the external controller. A control unit in the external pump module receives the ECG signal and triggers balloon inflation during systole. Active balloon deflation is performed by the pump during diastole. Balloon inflation may also be performed using a hydraulic system that contains a pressurized fluid tank that provides balloon inflation during systole, and a pressure release valve that allows balloon deflation during diastole. The fluid tank may be re-pressurized periodically, or a battery-operated compressor may be part of the unit that resides outside the patient's body.

Although a percutaneous approach is described above, the ventricular compression balloon device may be inserted via a minimally invasive surgical approach, using a small 4 cm subxiphoid incision to access and puncture the pericardium near the apex of the heart. A guidewire and tapered dilator may be inserted into the intrapericardial space anterior to the heart at the apical site, and advanced to exit the pericardium at a superior location on the left side of the pericardium. The dilator may then be removed from the patient, and the ventricular compression balloon catheter may be advanced over the guidewire into position across the left ventricle for cardiac assistance.

In some embodiments, the percutaneous ventricular assist device may comprise a balloon catheter that is inserted into the patient's pericardium near the apex of the heart, via a subxiphoid puncture site. A reservoir containing an elastomeric face is attached to the proximal end of the catheter. A four cm incision is performed to extend the subxiphoid puncture site, and the reservoir is implanted subcutaneously in the epigastric region of the abdominal wall. In the such devices, a single needle penetrates the patient's skin and the elastic face of the reservoir, to allow the pump unit external to the patient to inflate and deflate the balloon catheter, compressing the patient's ventricle during cardiac systole. Balloon inflation is triggered by the patient's ECG, as sensed in real time.

A minimum of two electrodes are required to obtain an ECG signal. In the previous device, the inflation needle formed one electrode, and a second electrode consisted of a surface electrode with an adhesive patch for skin attachment on the patient's abdomen or thorax. ECG signal obtained from a needle inserted through body tissue is superior ECG signal obtained from a surface electrode as the needle is less susceptible to motion artifacts and noise than a surface electrode. The proposed design incorporates one, two or more electrodes integral to the implantable reservoir, with a conductive mesh extending from each electrode to provide an expanded target to accommodate needle placement. The dimensions of the opening in the mesh is an interference fit with the circumference of the needle; such that upon needle insertion, the mesh applies compressive force against the outer surface of the needle, ensuring optimal ECG signal conduction. The needle may contain a series of bulbs or barbs to facilitate anchoring in the mesh component of the target electrode, preventing inadvertent needle detachment.

The body of the reservoir may be constructed of an implantable polymer material such as polycarbonate or polyvinyl chloride. The electrodes may be constructed of conductive metal such as stainless steel. If a single electrode is incorporated into one reservoir, the electrode may be a metallic ring attached to the outer diameter of the polymer reservoir. IF two electrodes are incorporated into a single reservoir, one electrode may be attached to the outer diameter of the reservoir, and the other electrode may be a small diameter concentric metal ring attached to the elastomeric face of the reservoir. A stainless-steel mesh may extend radially inward from the outer electrode towards the inner electrode, with a circumferential gap existing between the inner edge of the mesh and the outer edge of the inner electrode, to act as an insulator between the two electrodes. Alternatively, the two electrodes may be formed by two diametrically opposed arcs on the outer diameter of the reservoir, with the steel mesh extending between the two ends of each arc, preserving a non-conductive area between the two conductive mesh regions. A combination of multiple electrodes on multiple reservoirs may be applied; for example, two electrodes may reside on one implanted reservoir, and a single electrode may reside on a second implanted reservoir to yield a three-lead EKG sensing array.

In an additional embodiment of the invention, the circuit board receiving the EKG signal and controlling activation of the external pump unit is positioned in the reservoir. The signal from the control board is transmitted to the external pump unit via fiberoptic transmission, ensuring minimal signal noise due to patient motion. A fiberoptic connection consisting of a circumferential array around one of the inflation needles mates with a corresponding circular array in the circuit board. A funnel guide is incorporated into the inner concentric electrode of the reservoir, to ensure that needle insertion results in coaptation of the respective fiberoptic arrays on the needle and the control board in the reservoir. The two needles inserted through the mesh electrodes carry current from the external unit to power the circuit board inside the reservoir.

In a first aspect, the present invention provides a cardiac assist system comprising a pneumatic effector configured to be implanted beneath a patient's pericardial sac and over a myocardial surface, typically overlying the patient's left ventricle. The system further comprises an implantable port configured to receive a percutaneously introduced cannula, where the cannula supplies a driving gas to the pneumatic effector. Typically, the pneumatic effector may be a balloon located near a distal end of a catheter or other tubular body, where the implantable port is connected to the catheter or other tube near a proximal end.

The cardiac assist system further comprises an external drive unit which includes a pump assembly and control circuitry. The pump assembly includes at least one pump for delivering a gas, typically ambient air, to the cannula. The control circuitry is typically configured to operate the pump to actuate the pneumatic effector in response to the patient's sensed heart rhythm. Usually, the connecting tube has a pump end which is attachable to the pump of the pump assembly and a cannula end attached to the cannula.

In particular embodiments, the pneumatic effector may comprise an inflatable bladder, such as a medical balloon, typically a non-distensible medical balloon on a catheter, where the balloon is configured to sit over the left ventricle from the patient and beneath the inner surface of the pericardial sac. The balloon will typically have a volume, when fully inflated, in a range from 50 ml to 200 ml, typically from 76 ml to 125 ml. In other instances, the pneumatic effector may comprise some other pneumatically actuable mechanical device, such as a piston and cylinder arrangement.

In other instances and examples of the present invention, the implantable port may comprise a needle-penetrable septum, where the cannula comprises a needle or other sharpened tube or hollow probe configured to percutaneously penetrate the patient's tissue overlying the septum, typically the abdominal wall, and to further penetrate the septum to fluidly connect the pump assembly and the external drive unit with the interior of the port so that the air or other gas may be delivered under pressure to inflate or otherwise actuate the pneumatic effector.

In specific instances, the septum will have an area which is sufficiently large to provide multiple sites for needle penetration. This is a particular advantage when a percutaneous insertion site becomes infected. By having multiple needle penetration sites, the needle may be removed from an infected area, the patient treated, and a new or sterilized needle introduced to the implantable port through an alternate site on the septum. In this way, neither the implantable port nor the pneumatic effector need to be explanted or otherwise significantly disturbed in order to treat the infection.

In alternate embodiments, however, the implantable port may comprise a mechanical valve for receiving the needle or other cannula. Such mechanical ports are well known for hemodialysis access and other purposes. See, for example, U.S. Pat. No. 6,120,492, the full disclosure of which is incorporated herein by reference.

In still further embodiments, the systems of the present invention will further comprise at least one electrocardiogram (ECG) electrode located and configured to detect the patient's cardiac rhythm. The ECG electrode may be located externally as with conventional ECG detection systems, and may comprise one, two, three, four, or more external electrodes. Conveniently, however, one or more ECG electrodes may be incorporated into the cardiac assist system. For example, the electrodes may be provided by or incorporated into the needle or other cannula used to access the implantable port. Alternatively or additionally, one or more ECG electrodes may be located on or coupled to the implantable port itself. For example, one, two, three, four, or more ECG electrodes may be attached to an exterior surface of the port housing, the port septum or other membrane, or elsewhere on the port. Further alternatively or additionally, one or more ECG electrodes may be located on the connecting tube and/or on the pneumatic effector itself.

In systems having ECG electrodes, the external drive unit will typically further comprise ECG circuitry in order to detect cardiac rhythm and synchronize actuation of the pump assembly with the cardiac rhythm. When the ECG electrode(s) are present on any portion of the implantable port or connecting tube, electrical conductors may be provided in or through the needle or other cannula in order to deliver the electrical signals to the ECG circuitry. When the needle or other cannula itself comprises the ECG electrode, the needle or other cannula may be connected to the ECG circuitry through a conductor in the tube or other structure which connects the cannula to the external electrode. Conventional external ECG electrodes may be connected to the external controller by conventional ECG leads.

The control circuitry in the external drive unit will typically be configured to actuate the pneumatic effector in synchrony with the patient's cardiac rhythm as measured by the ECG. For example, the control circuitry may be configured to actuate the pneumatic effector at each occurrence of an R wave peak. Often, the control circuitry will be further configured to detect abnormal cardiac rhythms. For example, the control circuitry may compare the time between successive individual R peaks and determine the occurrence of an abnormal cardiac rhythm based upon time increases or decreases by more than a predetermined threshold percentage, such as 300 percent, usually 250 percent. Alternatively or additionally, the control circuitry may compare the time between successive cumulative R peaks and determine whether an abnormal cardiac rhythm exists based upon an aggregate variability exceeding a predetermined threshold percentage, typically 300 percent, usually 250 percent.

When the control circuitry detects an abnormal cardiac rhythm, it may take any of several actions. For example, the control circuitry may simply stop actuation of the pneumatic effector until the cardiac rhythm returns to a normal pattern. Alternatively, the control circuitry may actuate the pneumatic effector at a predetermined fixed rate, typically a fixed rate in the range from 50 beats per minute (bpm) to 80 bpm and continue such actuation until a normal cardiac rhythm is reestablished. Further alternatively, the control circuitry may be configured to actuate the pneumatic effector at a "proportionally" modified rate relative to the patient cardiac rhythm when the abnormal cardiac rhythm is detected. That is, while the actuation of the pneumatic effector would typically be at 1:1 ratio when the cardiac rhythm is normal, when an abnormal cardiac rhythm is detected, the rate may be changed to another ratio. For example, if the patient experiences an abnormally high heart rate (tachycardia), then the rate at which the pneumatic effector is triggered may be decreased. The pneumatic effector may be triggered once for every two heartbeats (1:2), once for every three heartbeats (1:3), or the like.

In still further embodiments, the pump assembly of the cardiac assist system may be configured to alternately deliver the driving gas to the pneumatic effector and to withdraw the driving gas from the pneumatic effector. Each cycle of deliver and withdrawal will correspond to a single trigger event from the control circuitry of the external controller. The cycle of pump delivery and pump withdrawal will correspond to the patient's heartrate as detected from the ECG, with a single cycle typically lasting about one second for a patient with a heartrate of 60 bpm. It will be appreciated that such rapid inflation and deflation requires a fast-acting system, and the available gas delivery volumes, fluid transmission lumen dimensions, and the like, will need to conform to the needed inflation and deflation times. To achieve the rapid delivery and extraction times, the fluid being delivered will typically be a gas, usually being ambient air.

The pump assembly may take any one of a variety of configurations for delivering and withdrawing the fluid to the pneumatic effector. For example, the pump assembly may include a single pump which operates in a single flow direction, further comprising valving necessary to divert the gas from an inflation direction to a deflation direction. Alternatively, the pump assembly may comprise a pair of pumps, one operating in a fluid delivery direction and the other operating in a fluid extraction direction. It will be further appreciated that the pump assembly may connect to either a single cannula which provides for both fluid delivery and fluid extraction from the implantable pump. Alternatively, the pump assembly may be connected to a pair of cannulas, one for delivering the inflation fluid and one for extracting the inflation fluid.

In a second aspect, the present invention provides a method for assisting cardiac function in a patient suffering from heart failure. The method may comprise detecting the patient's ECG to determine a cardiac rhythm. An implanted port within the patient is percutaneously accessed with a cannula, and a driving gas is delivered through the cannula to the port connected then delivered to a pneumatic effector implanted over the patient's left ventricle. Delivery and extraction of the driving gas is synchronized with a sensed cardiac rhythm to cause the pneumatic effector to compress the heart at a rate which generally matches the patient's natural cardiac rhythm.

In particular embodiments, the pneumatic effector will be implanted beneath the patient's pericardial sac and over a myocardial surface. In further particular embodiments, the pneumatic effector will be on a cardiac assist catheter which enters through the pericardium at an entry location and, in some instances, has a distal tip which passes out through the pericardium at an exit location. An anchor, such as a small anchoring balloon, may be provided on the distal tip of the cardiac assist catheter in order to stabilize the pneumatic effector at a desired position in the pericardial sac.

In still further particular embodiments, the ECG may be detected in a variety of ways. For example, one or more ECG electrodes may be located on the implanted port, on the implanted pneumatic effector, or elsewhere on the implanted portion of the system. In such instances, a signal from the implanted ECG electrode(s) may be delivered to the ECG circuitry in the external controller using the cannula as a percutaneous transmission element or conductor. In other particular embodiments, the cannula, or a plurality of cannulas, may themselves act as the ECG electrodes after they are percutaneously introduced to the implanted port. In still other particular embodiments, the ECG signal may be measured by one or more external electrodes attached to the patients in a conventional manner. It will be appreciated that single channel ECG may be used, but preferably at least two-channel ECG will be employed, preferably three-channel ECG, four-channel ECG, or greater. Electrodes may also be placed on the implanted pneumatic effector to provide cardiac pacing in the event of bradycardia in the patient or cardiac defibrillation in the event of ventricular tachycardia, ventricular fibrillation or asystole in the patient.

The methods of the present invention further comprise optionally detecting an abnormal cardiac rhythm. The abnormal cardiac rhythm will be determined based on the measured ECG, and the presence of an abnormal cardiac rhythm will typically result in stopping or modifying the operation of the pneumatic effector. For example, the driving gas may be stopped when an abnormal cardiac rhythm is detected. Alternatively, a delivery rate of the driving gas may be changed when an abnormal cardiac rhythm is detected. In particular, the driving rate may be reduced in the presence of a rapid heartbeat (tachycardia) or increased in the presence of a slow heartbeat (bradycardia).

The methods of the present invention further comprise protocols for treating the patient should the tissue access site become infected. In such cases, the needle or other cannula may be withdrawn from the tissue tract, the tissue tract treated for infection, and the cannula (either disinfected or a new cannula) reintroduced to the implanted port, typically through a different access route. For example, for septum-type ports, the cannula may be introduced to a different region of the part through a new tissue tract in non-infected tissue.

In a third aspect, the present invention provides an implantable cardiac assist catheter for use with an external drive unit, the implantable cardiac assist catheter comprises a catheter body having a proximal and a distal end. A pneumatic effector is attached to the distal end of the catheter body and is configured to be implanted beneath a patient's pericardial sac and over a myocardial surface overlying the patient's left ventricle. An implantable port is attached at a proximal end of the catheter body and is configured to receive a percutaneously introduced cannula. The port is connected to supply a driving gas received from the cannula through a gas lumen in the catheter body to the pneumatic effector. By controlling the supply of driving gas to the implantable port, the pneumatic effector can be driven at a desired rate as controlled by the external drive unit.

In particular embodiments, the implantable cardiac assist catheter may comprise a distal tip having a guidewire lumen with an entry port and an exit port, where both ports are located distal to the pneumatic effector. Such "monorail" construction is advantageous as it allows the remainder of the catheter body to have only a single fluid delivery lumen, thus reducing the needed diameter of the catheter. Thus, the gas lumen and the catheter body will typically be the only lumen present between the proximal end of the catheter body and the pneumatic effector.

Optionally, the distal tip of the implantable cardiac assist catheter may further comprise an anchoring balloon or other anchoring structure. Such anchoring structures can be used by advancing the distal catheter tip outwardly through the pericardium. After the pneumatic effector is properly positioned, typically over the patient's left ventricle, the anchor may be deployed (e.g. by balloon inflation) to stabilize the catheter position for subsequent use.

In a fourth aspect, the present invention provides an external drive unit for use with an implantable cardiac assist catheter, such as the cardiac assist catheter just described. The external driving unit comprises a pump assembly and control circuitry. The control circuitry is typically configured to operate the pump assembly to actuate a pneumatic effector on the implantable cardiac assist catheter in response to the patient's sensed heart rhythm.

In particular embodiments, the external drive unit may further comprise a connecting tube having a pump and connected to the pump assembly and a percutaneous port-connecting end configured to be removably attached to an implantable port fluidly connected to the pneumatic effector on the implantable cardiac assist catheter. In still further embodiments, the external drive unit may include ECG circuitry, where the ECG circuitry is configured to receive signals from at least one ECG electrode, located in any of the locations described previously, where the at least one ECG electrode is implanted to detect the patient's cardiac rhythm. Typically, the connecting tube will comprise at least one conductor electrically coupled to the cannula and configured to connect ECG electrodes to the ECG circuitry in the external drive unit.

In still further exemplary embodiments, the control circuitry of the external drive unit may be configured to actuate the pneumatic effector in synchrony with the patient's cardiac rhythm as measured by an ECG electrode. Actuation may be accomplished by detecting the occurrence of R wave peaks, as described generally above. The controls circuitry may be further configured to detect abnormal cardiac rhythms, and still further to stop or modify the actuation of the pneumatic effector in any of the ways described previously. The pump assembly may also have any of the configurations described previously with respect to the cardiac assist systems of the present invention.

For a fuller understanding of the nature and advantages of the present invention, reference should be made to the ensuing detailed description and accompanying drawings.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

FIG. 6 illustrates the details of how a needle or other cannula engages with conductive wires of an electrically conductive mesh embedded in the septum of an implantable port.

FIG. 7A illustrates a needle cannula having retaining bulbs along its length.

FIG. 7B illustrates a needle or other cannula in accordance with the present invention having retaining barbs along its length.

FIGS. 8A-8B illustrate an alternative access cannula constructed in accordance with the principles of the present invention and having fiber optic components for delivering cardiac rhythm information from an implantable port to an external drive unit.

FIG. 9 illustrates an implantable port suitable for use with the access cannula of FIGS. 8A and 8B.

FIG. 10A illustrates an alternate embodiment of the cardiac assist catheter having a balloon anchor at its distal tip.

DETAILED DESCRIPTION OF THE INVENTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiments being described.

Figure 1:
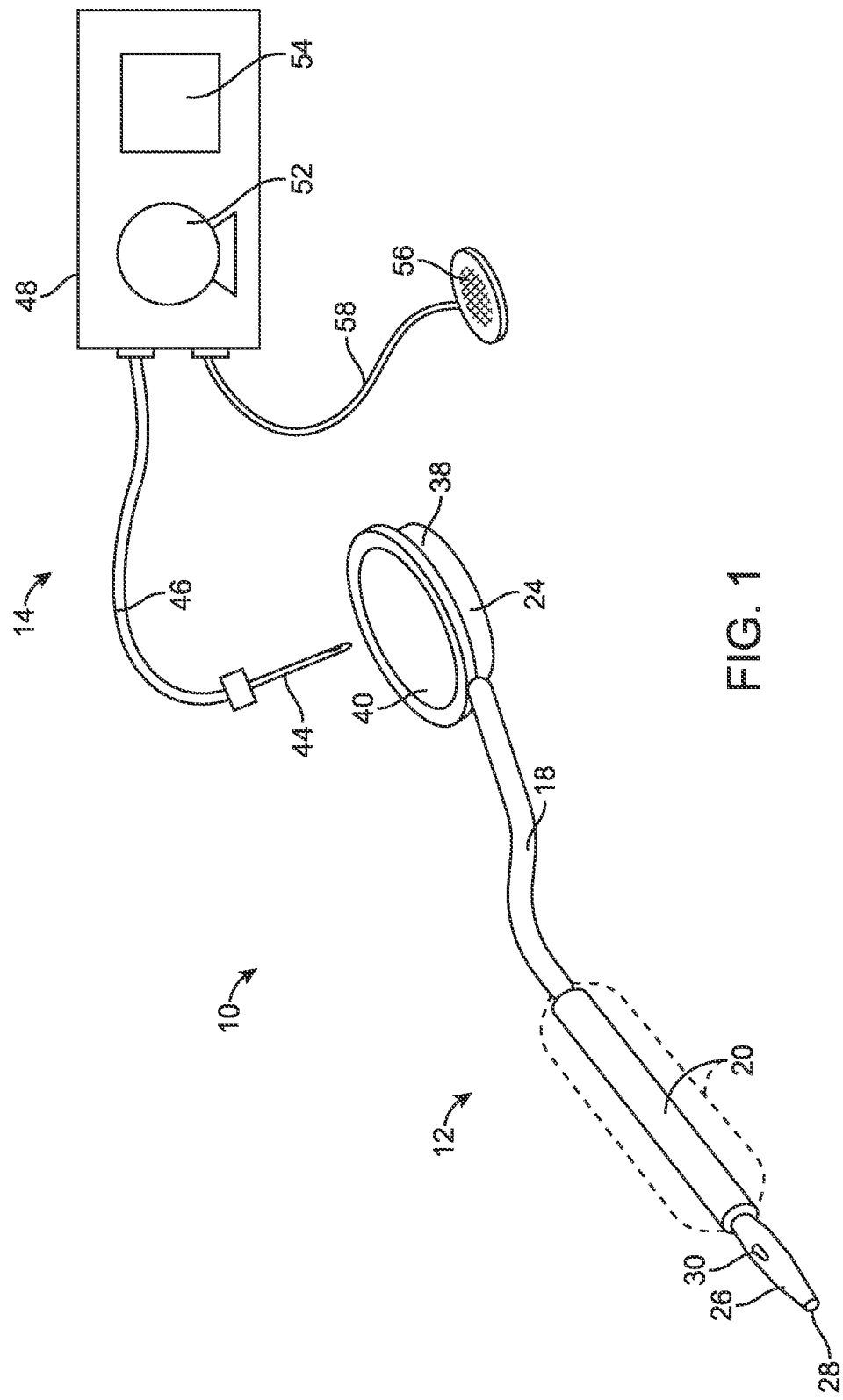
FIG. 1 is a perspective view of a cardiac assist system constructed in accordance with the principles of the present invention.

Referring now to FIG. 1, a cardiac assist system 10 constructed in accordance with the principles of the present invention may comprise a cardiac assist catheter 12 and an external drive unit 14. The cardiac assist catheter 12 typically includes a catheter body 18 having a balloon 20 or other pneumatic effector located at its distal end. An implantable port 24 is connected at a proximal end of the catheter body 18, and the body typically has a distal tip 26 with a short "monorail" guidewire lumen defined between a guidewire lumen entry port 28 and a guidewire lumen exit port 30. The length of the guidewire lumen will typically be from 0.5 cm to 3 cm, typically being from 1 cm to 2 cm.

The port 24 comprises a port body 38 or other enclosure having an opening on its upper surface. The opening is typically covered by a needle-penetrable septum 40.

The external drive unit 14 comprises a needle 44 or other cannula attached to a distal end of a connecting tube 46. The connecting tube is attached to a pump 52 within a console 48, and the console further includes control circuitry 54 for controlling the pump and other operations of the cardiac assist system 10. Optionally, the external drive unit 14 may further comprise an ECG pad 56 connected to the control circuitry 54 by a connecting cable 58. Typically, the pump, control circuitry and all other active components will be battery operated, and the external drive unit 14 will include a replaceable and/or rechargeable battery.

Figure 2A:
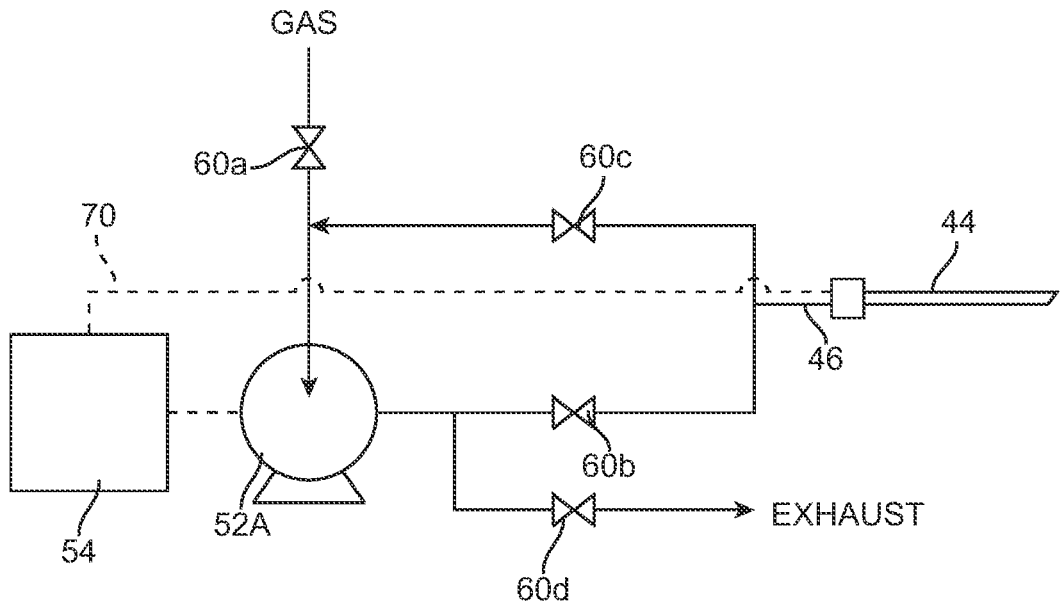
FIGS. 2A-2D illustrate different configurations of a pump assembly suitable for use with the cardiac assist systems of the present invention.

Referring now to FIGS. 2A-2D, the pump assembly 52 may comprise a variety of configurations. For example, as shown in FIG. 2A, a pump unit 52A, typically a diaphragm type of pump, is connected to cannula 44 by a series of valves $60_a$-$60_d$. The pump 50A will be configured to always run in a single direction, i.e. the inlet will always receive gas and the outlet will always deliver gas. To deliver gas to the cannula 44, valve $60_a$ will be open allowing ambient air to flow to the pump 50A. The ambient air is delivered out of the outlet of the pump to valve $60_b$ which is open. When delivering gas to the cannula, valves $60_c$ and $60_d$ will be closed. Gas continues to be delivered until the pneumatic effector 20 is inflated, at which time the valves $60_a$-$60_d$ are reversed. That is, gas inlet valve $60_a$ is closed and return bypass valve $60_c$ is opened, allowing gas to be extracted through the cannula 44 and delivered by the pump 52A through an open exhaust valve $60_d$. By reversing the open/closed status of valves $60_a$-$60_d$, the pump can be caused to first deliver gas through the cannula and then extract gas through the cannula without reversing operation of the pump 52A.

As also shown in FIG. 2A, an ECG lead line 70 may be provided between the cannula 44 and the control circuitry 54 of the external drive unit 14.

Figure 2B:
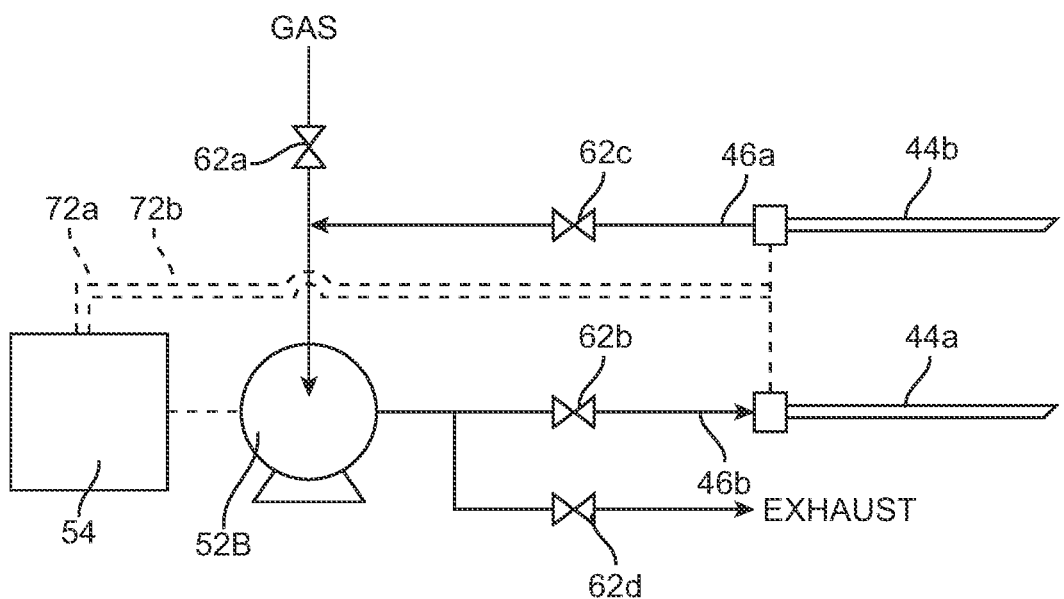
Figure 2C:
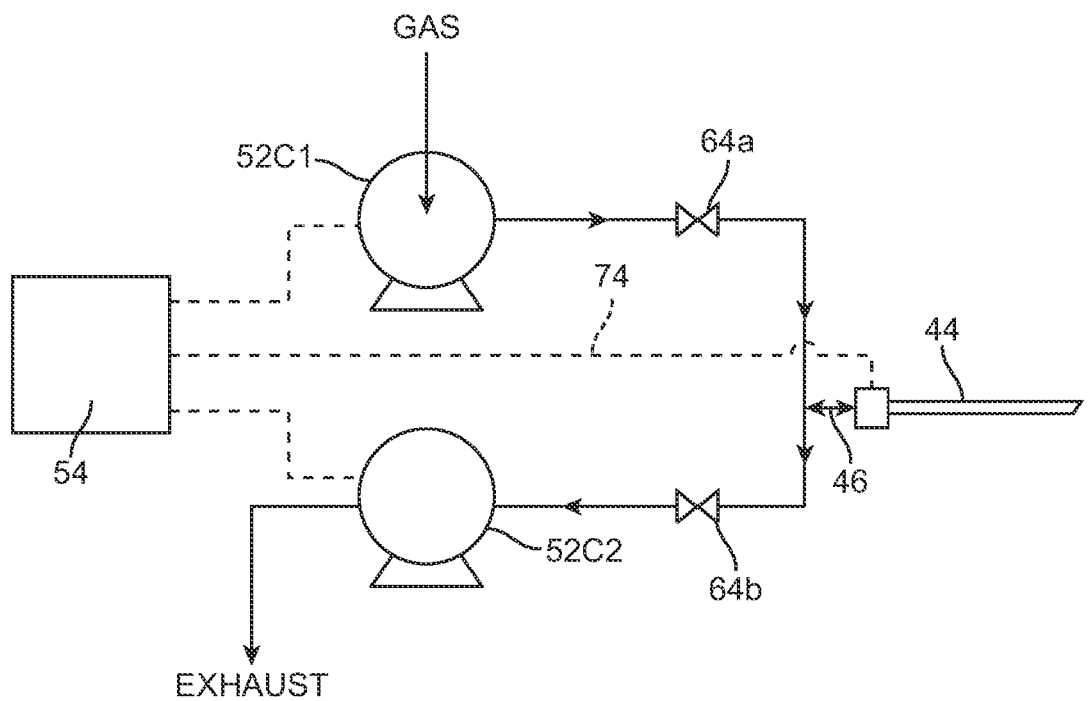
Figure 2D:
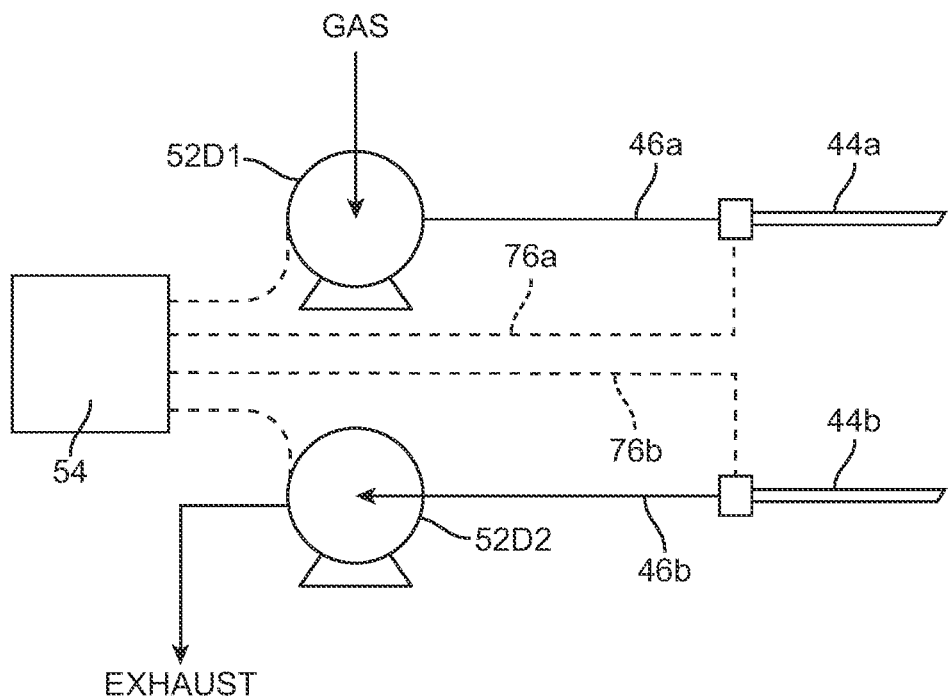

Referring now to FIG. 2D, a single pump 52B may be used with a pair of cannulas 44a and 44b. Valves $62_a$-$62_d$ will be used to reverse gas flow between the cannulas. In particular, by opening valve $62_a$ and valve $62_d$, ambient air may be delivered to gas delivery cannula $44_a$. By then closing valves $62_a$ and $62_b$, and opening valves $62_c$ and $62_d$, gas may be extracted through cannula 44b and out the exhaust valve $62_d$. Inflow and outflow of gas may be cycled by reversing the status of the valves in a manner similar to the valves of FIG. 2A.

In FIG. 2B, each cannula 44a and 44b has a separate ECG lead 72a and 72b connected to the control circuitry 54 of the external drive unit 14.

Referring now to FIG. 2C, a pump assembly 52 comprising two pumps 52c1 and 52c2 will be described. Control circuitry 54 actuates the first pump 52c1 to deliver ambient air through valves $64_a$ and then through cannula 44, while return valve 64b remains closed. After the pneumatic effector is fully inflated or otherwise actuated, valve 64a will be closed and the pump typically stopped. Return valve 64b will then be opened and pump 52c2 actuated to exhaust gas through the cannula 44 and out through the exhaust line, as illustrated. Operation of the two pumps and valves may be periodically reversed in order to cycle delivery and exhaust gas to and from the implanted port at a desired rate.

As also shown in FIG. 2C, an ECG lead line 74 may be provided between the cannula 44 and the control circuitry 54 of the external drive unit 14.

Referring now to FIG. 2D, a fourth pump assembly configuration will be described. This assembly comprises two pumps 52d1 and 52d2. Each pump, in turn, is connected to a single cannula 44a and 44b, respectively. While valving will typically be provided, no valves are theoretically necessary in order to cycle the system between gas delivery through pump 52d1 and cannula 44a and gas extraction through cannula 44b and pump 52d2, this may be achieved by simply starting and stopping the pumps at alternate times during the cycle.

As also shown in FIG. 2D, each cannula 44a and 44b is connected to the control circuitry 54 by an ECG lead 76a and 76b, respectively.

Figure 3A:
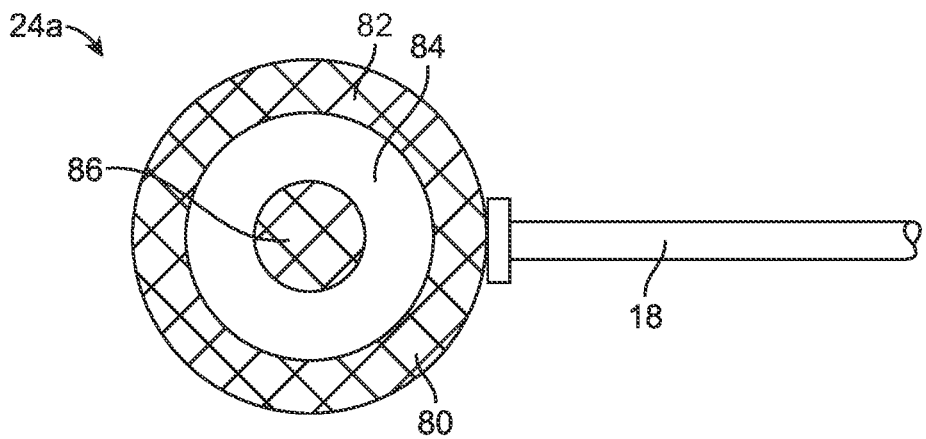
FIGS. 3A-3B illustrate a first implantable port configuration constructed in accordance with the principles of the present invention.
Figure 3B:
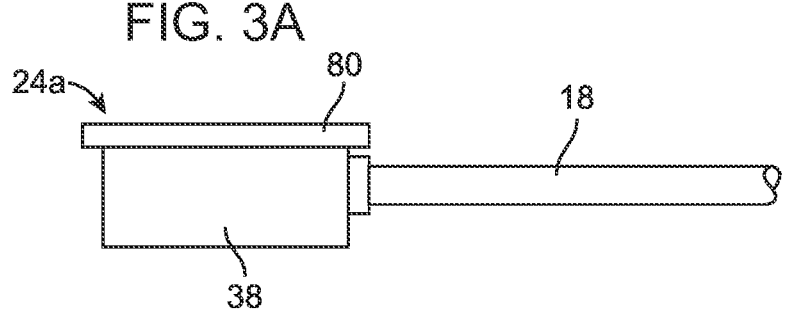

Referring now to FIGS. 3A and 3B, a first implantable port embodiment 24a is illustrated. FIG. 3A is a top view of the port where the top surface is typically oriented "anteriorly" toward the skin of the patient after it is implanted. A ring electrode 80 is attached to the outer circumference of the implantable port 24a and may optionally act as an ECG electrode. A circumferential band of metallic mesh 82 may be positioned over the outer perimeter of the upper surface of the port, typically over a needle-penetrable septum 84. A second, smaller inner ring electrode 86 may also be provided on an upper surface of the septum. The outer mesh electrode 82 is electrically insulated from the inner electrode 86 by the nonconductive septum material. Thus, first and second metal cannulas may be introduced through the inner and outer electrodes to provide for separate connections for a two-lead EKG signal detection. The ECG electrodes, themselves, may be located on the body of the port 44a or elsewhere in the implantable system. Internal conductive wiring will be provided between the ECG electrode(s) and the mesh electrodes 82 and 86.

Figure 4A:
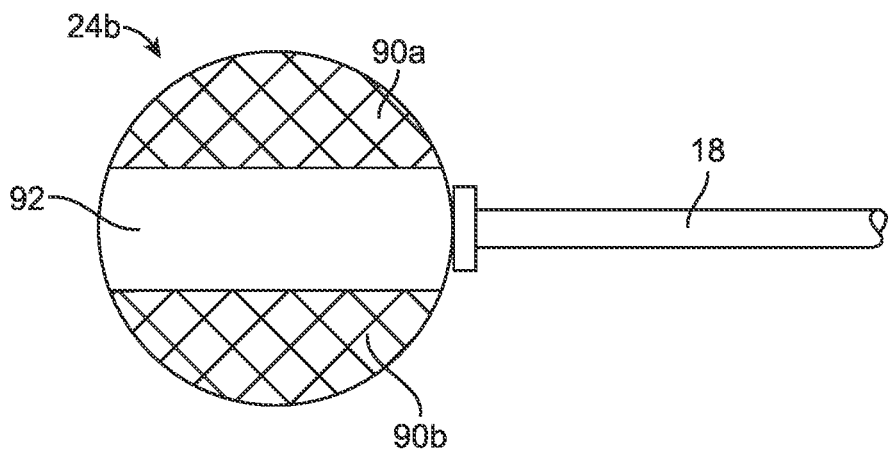
FIG. 4A-4B illustrate a second implantable port embodiment constructed in accordance with the principles of the present invention.
Figure 4B:
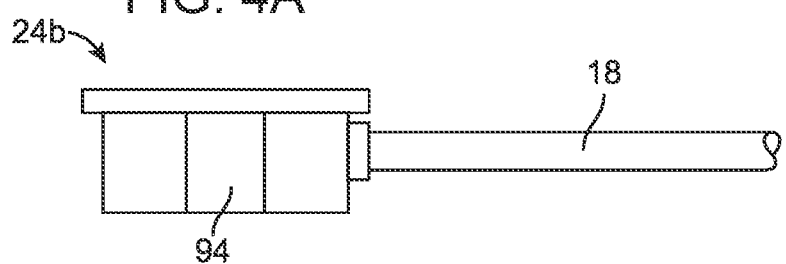

Referring now to FIGS. 4A and 4B, an alternative implantable port 24b is illustrated having first and second arcuate mesh electrodes 90a and 90b formed on an upper surface of a needle-penetrable septum 92. As shown in FIG. 4B, a first electrode 94a may be positioned on an outer perimeter of the port body with an internal connection to one of the two arcuate mesh electrodes. A second electrode (not seen in FIG. 4B) is located on the opposite face of the port body and may be connected to the other of the arcuate mesh electrodes in order to provide for separate cannula connections to each of the ECG electrodes.

Figure 5A:
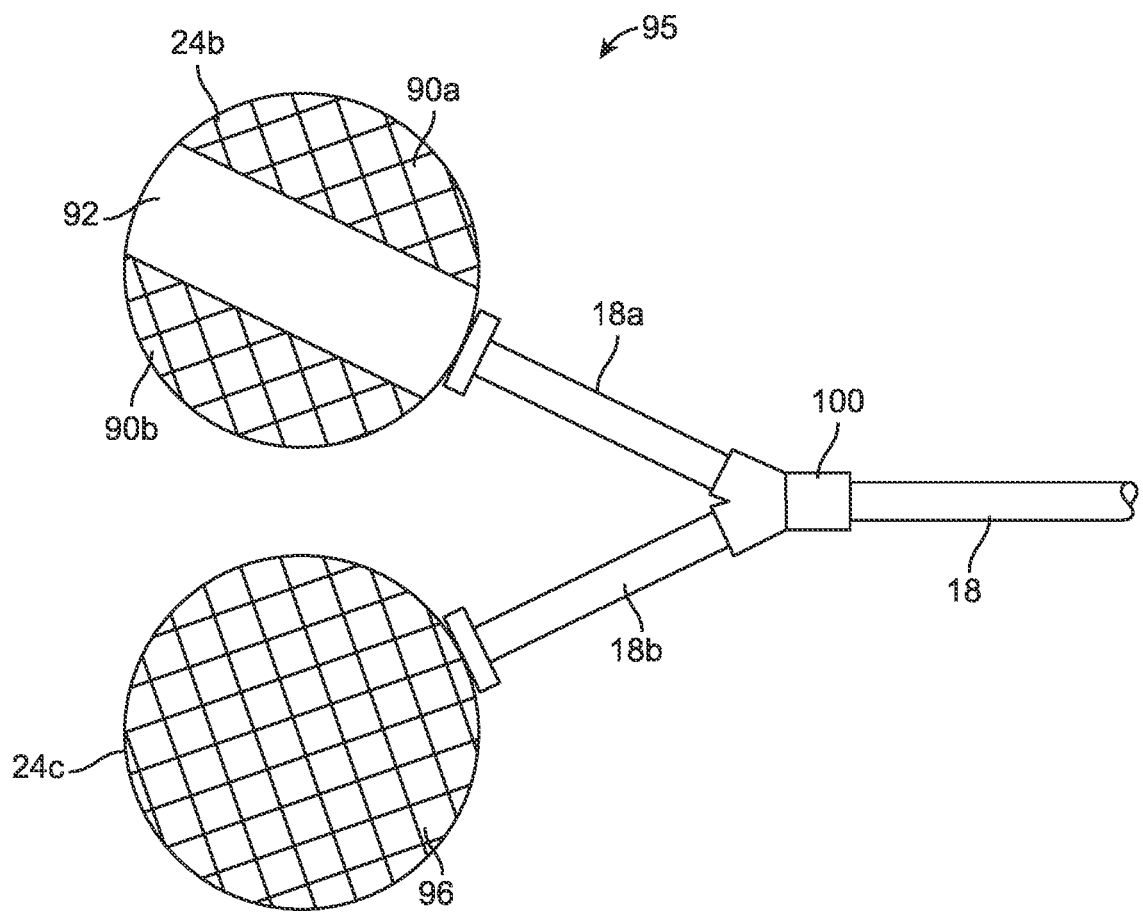
FIG. 5A-5B illustrate a third implantable port configuration constructed in accordance with the principles of the present invention.
Figure 5B:
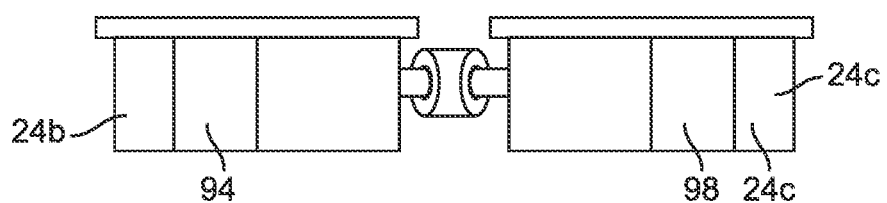

A still further implantable port assembly 95 is illustrated in FIGS. 5A and 5B. The port assembly 95 includes a first port 24b which may be identical to that described previously with respect to FIGS. 4A and 4B. A second port 24c may have a single mesh electrode covering the entire surface of an underlying needle-penetrable septum. The mesh electrode 96 may be connected to any ECG electrode, typically being connected to an electrically conductive portion of the port body. The ports 24b and 24c are connected together through catheter portions 18a and 18b through a y-connector 100 to a common catheter body 18 which may be connected to the pneumatic effector as described previously with regard to FIG. 1.

FIG. 6 illustrates how the cannula 14 forms an electrical connection with the wires of a mesh electrode. In particular, the mesh electrodes comprise orthogonally arranged conductive wires 102a and 102b. Small square-shaped cells are formed where the wires 102a and 102b cross over. The dimensions of the cells are chosen so that they are smaller than the diameter of the cannula so that, when inserted through the wire mesh, the wall of the cannula 14 will necessarily contact all four wire which define a single cell. In this way, good electrical contact is assured.

Referring now to FIG. 7A, the cannulas may be modified to enhance retention when they are inserted through the septum of the implantable ports, particularly through the wire mesh electrode structures on such septum. In particular, as shown in FIG. 7A, a needle structure 106 may have a series of bulbs 108 which help the needle resist accidental extraction from the mesh. Similarly, as shown in FIG. 7B, needle 110 may have a series of barbs 112 which resist needle extraction.

Referring now to FIGS. 8A, 8B, and 9, an optical system for delivering ECG information from an implantable port to the external drive unit will be described. As shown in FIG. 8A, a needle assembly 120 comprises a needle 122 having a plurality of optical fibers 126 embedded axially in a sheath 128. As shown in FIG. 8B, the optical fibers 126 are exposed in a distal surface of the sheath 128. As shown in FIG. 9, an implantable port 130 may be modified to receive the needle assembly 120 in a manner which transmits optical information to the optical fibers 126. In particular, the needle assembly 120 may be inserted through septum 132 of the port. An outer surface of the sheath 128 engages wires of a niche embedded in the septum 132. A distal surface of the sheath 128 engages an upper surface of a circuit board 140. The circuit board 140 comprises a plurality of optical emitters (not shown) configured to deliver light to the optical fibers 126 of the needle assembly 120. The needle 122 will pass through a hole or aperture 142 in the circuit board to permit the face of the sheath to engage the circuit board. A funnel 144 is provided to assist in proper alignment of the needle with the aperture. ECG electrodes 146a and 146b on an exterior of the port 130 are connected to the circuit board 140. Circuitry on the circuit board extracts ECG information from the electrodes, converts that information to optical energy which is delivered by the optical emitters to the optical fibers 126. The light is transmitted by the optical fibers to the external drive unit where it is converted back into electronic information suitable for controlling the system as described previously.

Figure 10:
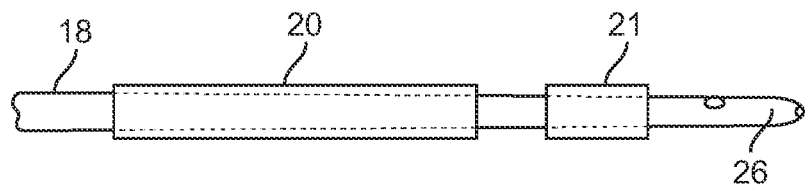
FIG. 10 illustrates the cardiac assist system of FIG. 1 implanted in a patient.
Figure 10:
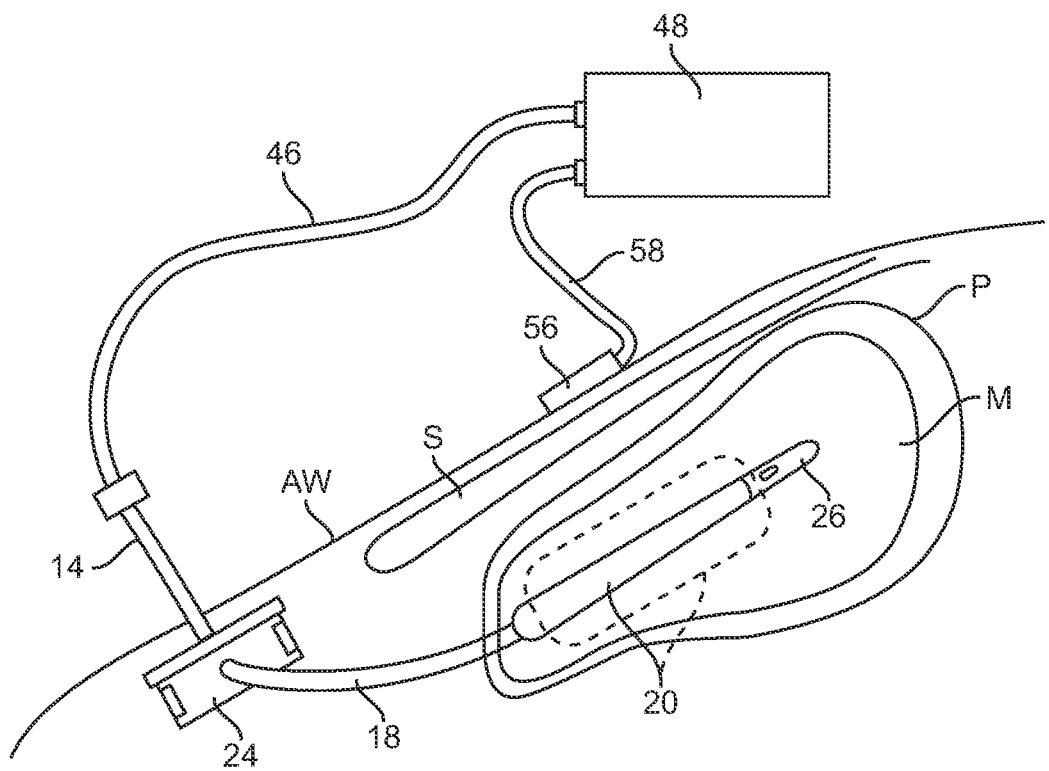

Referring now to FIG. 10, the cardiac assist system 10 of FIG. 1 may be implanted in a patient as illustrated. In particular, the balloon or other pneumatic effector 20 is introduced into the pericardial sac between an inner surface of the pericardium P and an outer surface of the myocardium M. The pneumatic effector 20 will preferably be located generally over the left ventricle so that inflation or other actuation of the effector compresses the left ventricle, as shown in broken line in FIG. 10. Port 24 is connected to the balloon by catheter body 18 and accessed percutaneously by cannula 14. The external drive unit 48 delivers actuating gas through connecting tube 46 and cannula 14 to the port 24 in order to actuate the pneumatic effector, typically by inflating and deflating a balloon. ECG is measured by the ECG pad 56 which is connected to the external drive unit by cable 58. Optionally, other ECG signals may be measured by electrodes on the implantable port 24 or elsewhere in the system.

Figure 11:
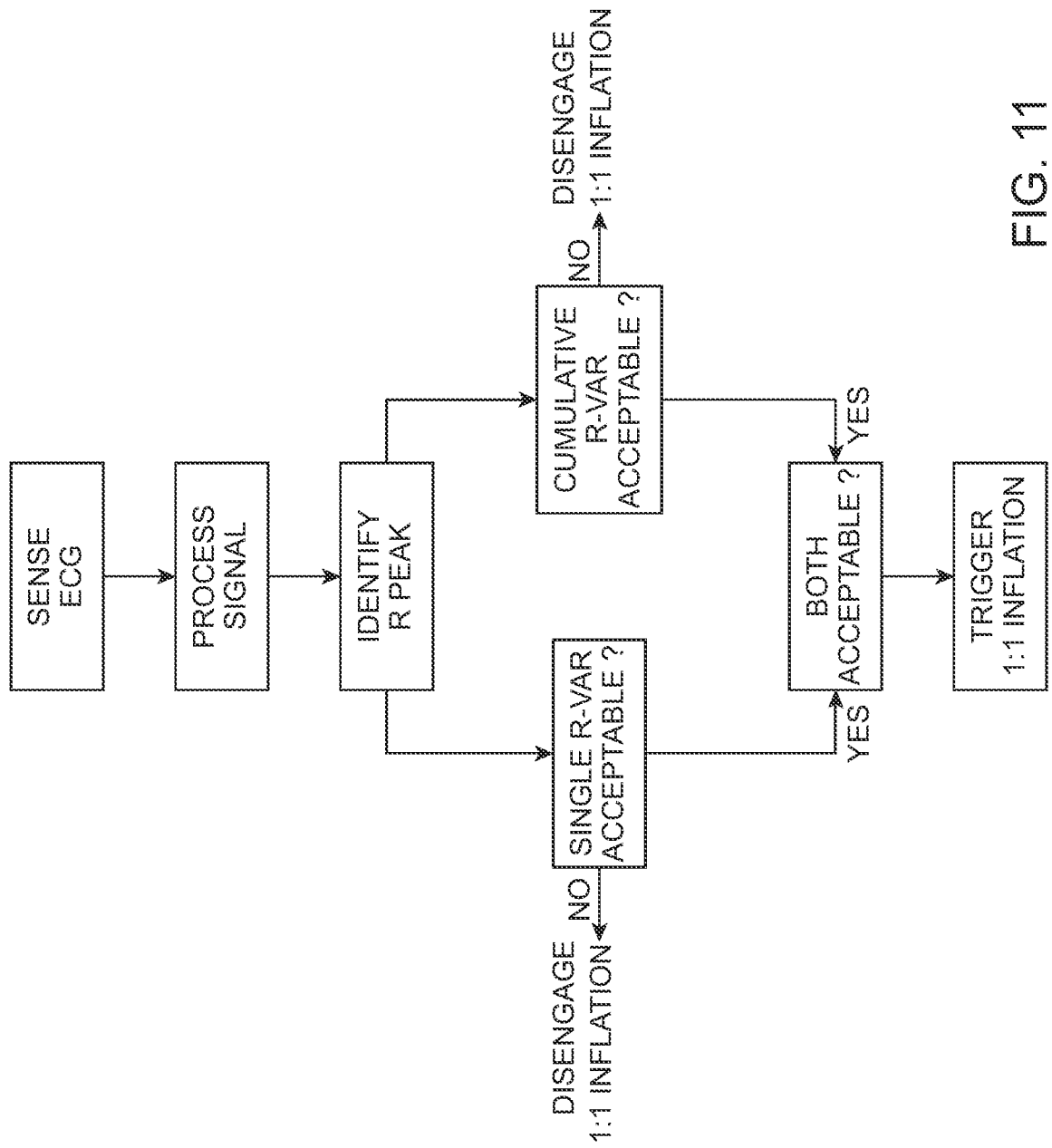
FIG. 11 is a logic flow diagram illustrating operation of the external drive unit of the cardiac assist system of the present invention.

Referring now to FIG. 11, an exemplary protocol for operating the pneumatic effectors of the present invention will be described. The patient's ECG is measured using any of the ECG electrodes described previously. The ECG measurement circuitry is typically incorporated into the external drive unit and operates on well-known ECG measurement principles. The raw ECG principles will undergo processing, typically digital processing for removing motion artifacts from the signal, and then the processed signal is scanned to determine the occurrence of signal artifacts associated with the patient cardiac rhythm, typically by measuring R peaks.

While the R peaks could be used to directly drive the pump assembly and pneumatic effector, typically the R peak pattern will be evaluated to determine if it is normal or abnormal. For example, the occurrence of successive single peak R values may be compared to determine whether they are increasing or decreasing in length. If the R-R peak interval remains constant within ±10 percent of the previous interval, cardiac rhythm will be considered normal and the trigger may be generated. Often, a second abnormality test will be applied to the R-R interval over a cumulative number of beats, for example 10 beats. If an R-R interval is larger than a threshold amount, for example 10 percent, of the mean R-R interval of the preceding 10 heart beats, the cardiac rhythm is considered abnormal.

In the event an abnormal cardiac rhythm is detected, the system may take any one of a number of actions. For example, the system may shut down triggering of the pneumatic effector until the patient's native cardiac rhythm returns to normal. Alternatively, in the case of rapid heartbeat, the 1:1 synchronization between the natural heart rhythm and the triggering of the pneumatic effector may be altered, for example the effector may be triggered on every second natural beat (a 2:1 ratio), every third beat (a 3:1 ratio), or the like. Actuation of the pneumatic effector at a 1:1 ratio may be resumed as soon as the cardiac rhythm returns to normal.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

What is claimed is:

1. A cardiac assist system comprising:
   a pneumatic effector configured to be implanted to only a space beneath a patient's pericardial sac and over a myocardial surface overlying the patient's left ventricle and configured to selectively expand and contract within said space, wherein the pneumatic effector is elliptical in shape and has a length configured to extend along a major portion of the ventricular cavity;
   an implantable port configured to receive a percutaneously introduced cannula, wherein said port is connected to supply a driving gas received from the cannula to the pneumatic effector;
   an external drive unit including:
   (a) a pump assembly configured to alternately (i) deliver the driving gas to the pneumatic effector to expand the pneumatic effector during cardiac systole and (ii) withdraw the driving gas from the pneumatic effector to contract the pneumatic effector during cardiac diastole; and
   (b) control circuitry configured to operate the pump assembly to actuate the pneumatic effector in synchrony with the patient's cardiac rhythm as measured by an electrocardiogram (ECG); and
   a connecting tube having a pump end attachable to the pump assembly and a cannula end attached to the cannula.

2. The cardiac assist system of claim 1, wherein the control circuitry is configured to deliver the driving gas to the pneumatic effector at the start of the QRS complex or R wave peak of the measured ECG.

3. The cardiac assist system of claim 1, further comprising an anchor disposed distally of the pneumatic effector on a catheter body and configured to be deployed at the patient's pericardial sac to stabilize the pneumatic effector in position within the space beneath the patient's pericardial sac and over a myocardial surface overlying the patient's left ventricle.

4. A method for assisting cardiac function in a patient suffering from heart failure, said method comprising:
   detecting the patient's electrocardiogram (ECG) to determine a cardiac rhythm;
   percutaneously accessing an implanted port with a cannula;
   alternately delivering and withdrawing a driving gas through the cannula to the implanted port which is connected to a pneumatic effector implanted to only a space beneath the patient's pericardial sac and over a myocardial surface overlying the patient's left ventricle and to selectively expand and contract within said space, wherein the pneumatic effector is elliptical in shape and has a length configured to extend along a major portion of the ventricular cavity;
   wherein the alternately delivering and withdrawing of the driving gas is synchronized with the determined cardiac rhythm to cause the pneumatic effector to compress and decompress the heart at a rate which matches the cardiac rhythm.

5. The method of claim 4, wherein the ECG is detected with one or more electrodes located on the implanted pneumatic port.

6. The method of claim 4, wherein the ECG is detected with one or more electrodes located on the implanted pneumatic effector.

7. The method of claim 4, wherein the ECG is detected with the cannula acting as an ECG electrode.

8. The method of claim 4, wherein the ECG is detected with an external electrode.

9. The method of claim 4, further comprising detecting an abnormal cardiac rhythm.

10. The method of claim 9, wherein delivery of the driving gas is stopped when an abnormal cardiac rhythm is detected.

11. The method of claim 9, wherein a rate of one or more of the delivering or withdrawing the driving gas is changed when an abnormal cardiac rhythm is detected.

12. The method of claim 11, wherein the rate is below a rate of the detected cardiac rhythm.

13. The method of claim 12, wherein the rate is a predetermined fixed rate.

14. The method of claim 4, further comprising removing the cannula from the access site when an infection of the access site is observed.

15. The method of claim 14, further comprising treating the infection and replacing the cannula.

16. The method of claim 15, wherein the cannula is replaced through a different site to access the implaned port.

17. The method of claim 16, wherein the cannula comprises a needle and the port comprise a needle-penetrable penetrable septum and the different site is a different region on the septum.

18. The method of claim 4, wherein the implanted port is percutaneously accessed with the cannula through a subxiphoid puncture site.

19. The method of claim 4, wherein the pneumatic effector is disposed at a distal portion of a catheter body.

20. The method of claim 19, wherein the pneumatic effector is advanced through a subxiphoid puncture site.

21. The method of claim 19, further comprising advancing the catheter body toward the patient's pericardial sac to deploy an anchoring structure which maintains the pneumatic effector in position within the space beneath the patient's pericardial sac and over a myocardial surface overlying the patient's left ventricle.

22. An implantable cardiac assist catheter for use with an external drive unit, said implantable cardiac assist catheter comprising:
   a catheter body having a proximal end and a distal end, the catheter body being configured to be advanced through a subxiphoid puncture site and then across a patient's left ventricle;
   a pneumatic effector proximal of the distal end of the catheter body and configured to be implanted to only a space beneath a patient's pericardial sac and over a myocardial surface overlying the patient's left ventricle, wherein the pneumatic effector is further configured to selectively expand and contract within said space, and wherein the pneumatic effector is elliptical shape and has a length configured to extend along a major portion of the ventricular cavity; and
   an implantable port at the proximal end of the catheter and configured to receive a percutaneously introduced cannula, said port being connected to supply a driving gas received from the cannula through a gas lumen in the catheter body to the pneumatic effector.

23. The implantable cardiac assist catheter of claim 22, further comprising an anchor disposed distally of the pneumatic effector on the catheter body and configured to stabilize the pneumatic effector in position within the space beneath the patient's pericardial sac and over a myocardial surface overlying the patient's left ventricle.

24. The implantable cardiac assist catheter of claim 23, wherein a distal tip of the catheter comprises the anchor.

25. The implantable cardiac assist catheter of claim 24, wherein the distal tip is configured to be advanced through the patient's pericardium.

26. The implantable cardiac assist catheter of claim 24, wherein the anchor comprises an anchoring balloon.

27. The implantable cardiac assist catheter of claim 22, further comprising an anchor disposed distally of the pneumatic effector on the catheter body and configured to be deployed at the patient's pericardial sac to stabilize the pneumatic effector in position within the space beneath the patient's pericardial sac and over a myocardial surface overlying the patient's left ventricle.

28. An external drive unit for use with an implantable cardiac assist catheter, said external drive unit comprising:
   (a) a pump assembly configured to alternately (i) deliver the driving gas to a pneumatic effector of the implantable cardiac assist catheter during cardiac systole to expand the pneumatic effector and (ii) withdraw the driving gas from the pneumatic effector during cardiac diastole to contract the pneumatic effector,
      wherein the pneumatic effector is configured to be implanted to only a space beneath a patient's pericardial sac and over a myocardial surface overlying the patient's left ventricle, wherein the pneumatic effector is further configured to selectively expand and contract within said space, and wherein the pneumatic effector is elliptical in shape and has a length configured to extend along a major portion of the ventricular cavity; and
   (b) control circuitry configured to operate the pump assembly to actuate the pneumatic effector on the implantable cardiac assist catheter in synchrony with the patient's cardiac rhythm as measured by an electrocardiogram (ECG).

29. The external drive unit of claim 28, wherein the control circuitry is configured to deliver the driving gas to the pneumatic effector at the start of the QRS complex or R wave peak of the measured ECG.

30. The external drive unit of claim 28, wherein the pneumatic effector is stabilized in position within the space beneath the patient's pericardial sac and over a myocardial surface overlying the patient's left ventricle by an anchor coupled to the pneumatic effector and deployed at the patient's pericardial sac.

* * * * *